United States Patent [19]

Müller

[11] 4,212,823

[45] Jul. 15, 1980

[54] PROCESS FOR THE MANUFACTURE OF 3-AMINOPHENOLS BY DEHYDROGENATION OF 3-AMINOCYCLOHEXENONES

[75] Inventor: Werner H. Müller, Bremthal, Fed. Rep. of Germany

[73] Assignee: Hoechst Aktiengessellschaft, Frankfurt, Fed. Rep. of Germany

[21] Appl. No.: 707,016

[22] Filed: Jul. 20, 1976

Related U.S. Application Data

[63] Continuation-in-part of Ser. No. 542,423, Jan. 20, 1975, abandoned.

[30] Foreign Application Priority Data

Jan. 21, 1974 [DE]   Fed. Rep. of Germany ....... 2402695

[51] Int. Cl.$^2$ ...................... C07C 91/44; C07C 85/24
[52] U.S. Cl. .................................. 260/571; 260/574; 260/575
[58] Field of Search ................... 260/574, 575, 621 H, 260/571

[56] References Cited

U.S. PATENT DOCUMENTS

| | | | |
|---|---|---|---|
| 2,249,352 | 7/1941 | Fitch | 260/574 |
| 3,102,913 | 9/1963 | Werner | 260/574 |
| 3,801,651 | 4/1974 | Adolphen et al. | 260/621 H X |

OTHER PUBLICATIONS

Zymalkowski, et al. "Synthesis of bz-tetrahydroquinolines" in Chem. Abs. 15395g, 1960.
Sutter et al. "Monoethers of 1,2-dihydroxybenzene" in Chem. Abs. vol. 74, 1971, 3407g.

*Primary Examiner*—John Doll
*Attorney, Agent, or Firm*—Curtis, Morris & Safford

[57] ABSTRACT

3-Aminophenols are prepared by dehydrogenation at elevated temperature of 3-aminocyclohexenones. The compounds obtained are valuable intermediates for drugs, dyestuffs and herbicides.

9 Claims, No Drawings

PROCESS FOR THE MANUFACTURE OF 3-AMINOPHENOLS BY DEHYDROGENATION OF 3-AMINOCYCLOHEXENONES

This is a continuation-in-part of abandoned application Ser. No. 542,423 filed Jan. 20, 1975.

The present invention relates to a process for the manufacture of 3-aminophenols, which are valuable intermediates for drugs, dyestuffs and herbicides, by dehydrogenation of 3-aminocyclohexenones.

Hitherto, it has only been possible to prepare 3-aminophenols commercially by complicated methods involving aromatic substitution reactions, namely nitration, sulfonation and caustic fusion. 3-Diethylaminophenol, for example, which is used in the synthesis of rhodamine and oxazine dyes, is prepared from benzene by a process comprising five stages (benzene→nitrobenzene→m-nitrobenzene sulfonic acid→m-aminobenzene sulfonic acid→m-diethylaminobenzene sulfonic acid→m-diethylaminophenol).

N-ethyl-3-aminophenol—an important dye intermediate—is formed by caustic fusion of N-ethylmetanilic acid (prepared by sulfonation of N-ethylaniline or by monoethylation of metanilic acid) or by treatment of resorcinol with ethylamine at 190° to 195° C.

Unsubstituted 3-aminophenol is prepared according to one method by treating resorcinol with ammonia under pressure in the presence of ammonium chloride or sulfite and according to another method by fusion of metanilic acid with sodium hydroxide at temperatures above 250° C.

Resorcinol itself is obtained commercially only by a very complicated sulfonation caustic fusion process starting from benzene.

All these commercial processes for the preparation of primary, secondary and tertiary aminophenols comprise a nitration, sulfonation or caustic fusion step. This requires handling of highly corrosive concentrated nitric or sulfuric acid or molten sodium hydroxide at elevated temperatures which leads to difficult and expensive process technology and to environmental pollution by off-gas and waste-water streams. If the above processes are to be carried out in the future, environmental pollution control requires a laborious and expensive clean-up of the waste waters which contain an amount of sulfite and sulfate that is at least twice as high as the yield of the desired 3-aminophenol because of the caustic fusion. The waste waters are contaminated with organic materials such as phenols and, therefore, cannot be discharged even after removal of the mentioned salts but only after an additional biological degradation.

It is the object of the present invention to prepare 3-aminophenols by dehydrogenation of 3-aminocyclohexenones.

The 3-aminocyclohexenones suitable for dehydrogenation according to the invention can be obtained from aliphatic starting materials, for instance by cyclization of cyanoethylated ketones, by reacting enamines (Schiff's bases) with acrylic acid chlorides or by reacting the corresponding cyclohexanediones with ammonia, amines or ureas. Cyclohexanediones in turn can be readily prepared by cyclization of 5-oxo-carboxylic acid esters, i.e. again from an aliphatic starting material. This means that 3-aminophenols can be prepared exclusively from aliphatic starting materials without the environmental pollution problems linked to the nitration, sulfonation and caustic fusion necessary in the known processes.

When one mole of a cyclohexanediones

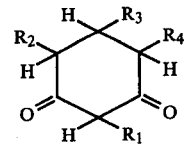

is reacted with one mole of an amine

3-aminocyclohexenones of the formula

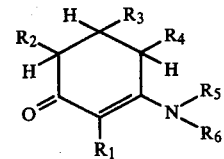

are obtained.

In the above formulae the radicals $R_1$ to $R_6$, which may be identical or different, have the following meaning: hydrogen; straight chain, branched or cyclic alkyl groups generally having up to 12 carbon atoms and optionally carrying substituents; aryl groups having from 6 to 14 carbon atoms and optionally being substituted. The radicals $R_5$ and $R_6$ may also form together an alkylene group having from 4 to 6 carbon atoms, which may be interrupted by an oxygen or a substituted nitrogen atom.

Suitable straight chain, branched or cyclic alkyl groups are especially methyl, ethyl, propyl, butyl, pentyl, hexyl, octyl, dodecyl, cyclohexyl and cyclododecyl. The alkyl groups preferably have up to 6 carbon atoms. They may carry as substituents, for example, halogen atoms, especially fluorine and chlorine, amino groups, hydroxyl groups, keto groups, carboxyl groups, carbamide groups or cyano groups, or optionally a carbalkoxy group having up to 6 carbon atoms, such as carboxymethyl ($COOCH_3$) or carboxyethyl ($COOC_2H_5$).

Suitable aryl groups are preferably, phenyl or naphthyl which may be substituted, for example, by halogen atoms, preferably fluorine and chlorine, alkyl groups having up to 6 carbon atoms, or trifluoromethyl, pentafluoroethyl or nitro groups. Further suitable substituents are alkoxy groups having up to 6 carbon atoms, for example methoxy or ethoxy.

By dehydrogenation of the 3-aminocyclohexenones 3-aminophenols of the formula

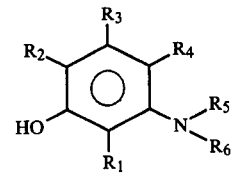

in which $R_1$ to $R_6$ have the aforesaid meaning are obtained.

When 2 moles of a cyclohexanediones of the formula

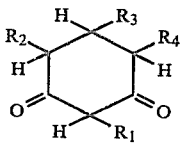

are reacted with 1 mole of a diamine, reaction products are obtained having twice the 3-aminocyclohexenone structure (cf. Examples 5 and 6). In the dehydrogenation according to the invention compounds of this type yield products containing two 3-aminophenol structures (cf. Examples 16 and 17).

Suitable diamines are (1) aliphatic diamines of the formula $H_2N-(CH_2)_n-NH_2$ in which n is in the range of from 2 to 12 and the substitution products thereof in which one hydrogen atom at each nitrogen atom or one or both hydrogen atoms at each carbon atom are replaced by radicals having the same meaning as defined above for $R_1$ to $R_6$; preferred diamines being ethylene diamine, propylene diamine, tetramethylene diamine, pentamethylene diamine, hexamethylene diamine, decamethylene diamine, dodecamethylene diamine, N,N'-dimethyl-tetramethylene diamine and N,N'-dimethyl-hexamethylene diamine;

(2) alicyclic diamines such as bis(aminomethyl)-cyclohexane or bis (aminocyclohexyl)-methane;

(3) aromatic diamines of the formula

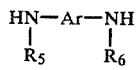

in which Ar represents an aromatic radical having from 6 to 14 carbon atoms and $R_5$ and $R_6$ have the same meaning as defined above, Ar preferably representing phenyl, biphenyl, or naphthyl; said aromatic radicals optionally being substituted by halogen, preferably fluorine and chlorine, alkyl groups having up to 6 carbon atoms, or trifluoromethyl, pentafluoroethyl, or nitro groups; or alkoxy groups having up to 6 carbon atoms, for example, methoxy or ethoxy; especially suitable aromatic diamines being phenylene diamine, benzidine and dianisidine;

(4) aromatic-aliphatic diamines, for example, xylylene diamine, methylene dianiline and bis(aminoethyl)-benzene.

The dehydrogenation of the 3-aminocyclohexenones can be carried out according to known methods, for example, by melting in the presence of a dehydrogenation agent, such as sulfur or selenium, or by heating in the presence of a dehydrogenation catalyst. Suitable dehydrogenation catalysts are, for example, platinum metals such as ruthenium, rhodium, palladium, osmium, iridium and platinum, or other metals such as copper, silver, gold, iron, cobalt and nickel.

The aforesaid catalysts are preferably supported on carrier materials such as carbon, aluminium oxide, silicic acid, magnesium oxide, calcium oxide, titanium oxide and asbestos, or a mixture of any two or more of the aforesaid materials, carbon and aluminum oxide being preferred. The catalyst contains in general from 0.1 to 20% by weight of metal, preferably from 0.2 to 10% by weight of metal, calculated on the carrier material.

The dehydrogenation can be carried out either in the liquid or in the gaseous phase.

When operating in the liquid phase an inert solvent which boils at a temperature in the range of from 150° to 270° C., for example, a hydrocarbon such as decahydronaphthalene or tetrahydronaphthalene, or an aromatic and aliphatic ether such as diphenyl ether, diethylene glycol diethyl ether, or triethylene glycol diethyl ether may be used. It is very advantageous to operate in the presence of substances acting as hydrogen acceptors, i.e. substances which absorb the hydrogen as soon as it is formed, since in this case the dehydrogenation takes place under relatively mild conditions. Suitable hydrogen acceptors are unsaturated compounds, for example, ethylene, propylene, heptene, octene, cyclohexene, styrene, α- and β-methylstyrene, stilbene, 1,1-diphenyl-ethylene, benzene, biphenyl, anthracene, acenaphthylene, crotonic acid, maleic acid, fumaric acid, cinnamic acid, muconic acid, as well as the esters thereof with alcohols having up to 6 carbon atoms; mesityl oxide, benzalacetone, benzalacetophenone, butendiol and the esters thereof with alcohols having up to 6 carbon atoms, maleic anhydride, coumarin, tolane, phenyl acetylene, butynediol and its esters with carboxylic acids having up to 6 carbon atoms.

Further suitable hydrogen acceptors are ketones such as benzophenone, cyclohexanone, benzoquinone; nitro compounds such as nitro-propane, nitrobenzene, p-nitrotoluene, o-nitrophenol, m-nitroacetophenone, o-nitroacetanilide.

When hydrogen acceptors of the aforesaid types are used, they may react with the aminophenols formed in the reaction to yield substituted aminophenols.

When the process is carried out in the gaseous phase, a carrier gas can be used, for example, nitrogen, carbon dioxide, argon, or hydrogen, or a readily volatile solvent, for example, water, ethanol, acetone, or diethyl ether, can be added to the starting material. One of the aforesaid hydrogen acceptors can also be added provided that it evaporates under the reaction conditions.

Depending on the type of the aminocyclohexenones used and on the reaction conditions applied, the dehydrogenation is carried out continuously or discontinuously at a temperature in the range of from 130° to 450° C. In general, the temperature is in the range of from 150° to 300° C., preferably 170° to 240° C. Normally, the dehydrogenation is carried out under reduced or atmospheric pressure, although dehydrogenation at elevated pressure, for example, up to 5 atmospheres, is likewise possible. In most cases the pressure will not exceed 20 atmospheres.

The dehydrogenation to 3-aminophenols of 3-aminocyclohexenones which are primary or secondary amines is particularly surprising in view of the unexpected absence of interfering condensation reactions. It had to be expected that intermolecular condensation of 3-aminocyclohexenone starting material or condensation of 3-aminocyclohexenone with the formed 3-aminophenol would occur, followed by dehydrogenation of said condensation products.

The 3-aminocyclohexenones prepared as described in Examples 1, 2 and 4 to 7 have not yet been disclosed in the literature. They can be used for making the 3-aminophenols according to the invention and are themselves light stabilizers.

The following examples illustrate the invention.

(A) PREPARATION OF 3-AMINOCYCLOHEXENE-2-ONES

Examples 1 to 7

0.2 mole of a cyclohexane dione as specified in Table 1 and 0.2 to 0.4 mole of a monoamine or 0.1 to 0.2 mole of a diamine in 200 ml of benzene were refluxed until 0.2 mole of water had separated in a water separator. When the benzenic solution was cooled or concentrated the respective enaminoketone separated. It was purified by recrystallization or distillation. The yield was from 50 to 95%.

(B) DEHYDROGENATION OF THE 3-AMINOCYCLOHEXENE-2-ONES

Examples 8 to 20

In a 250 cc three-necked flask, equipped with magnetic stirrer, thermometer and Claisen bridge, a mixture of 100 ml of solvent and 2 grams of a dehydrogenation catalyst (0.1 g Pd supported on 0.9 g of active carbon) was heated to from 150° to 220° C. while stirring and purging with nitrogen. A solution of the respective 3-aminocyclohexenone as specified in Table 2 in 20 to 50 ml of methanol was then added. Prior to the addition, the introduction of nitrogen was stopped. The hydrogen formed in the dehydrogenation was measured with a gasometer. The methanol was distilled off over the Claisen bridge and collected in a flask.

During the course of reaction the temperature was maintained at 180° to 220° C. When the addition of the amino-ketone was terminated, the mixture was maintained for a short while at 200° to 220° C. until the generation of hydrogen ceased. The reaction mixture was cooled while passing through nitrogen, the catalyst was filtered off and the solution distilled under reduced pressure. After the polyglycol ether fraction, the respective 3-aminophenol passed over, which in most cases crystallized in the receiver or was crystallized by the addition of diethyl ether or petroleum ether.

A known product was identified by its melting point and its NMR spectrum and an unknown product was identified by determination of the C, H and N content and by its NMR spectrum.

Table 2 summarizes in Examples 8 to 20 the dehydrogenation reactions yielding 3-aminophenols. The compounds obtained in Examples 12, 16, 17 and 20 have not yet been described in the literature.

TABLE 1

Part 1

| | starting material | | | reaction conditions | |
|---|---|---|---|---|---|
| Example | cyclohexane dione (1,3) (g) | amine structure | (g) | solvent (benzene) (ml) | dreaction time (h) |
| 1 | 33.0 |  | 25.0 | 200 | 5.0 |
| 2 | 22.0 | 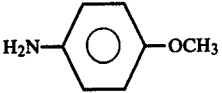 | 24.6 | 200 | 1.0 |
| 3 | 22.0 | 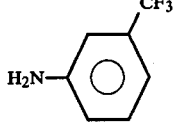 | 32.0 | 200 | 6.0 |
| 4 | 11.0 | 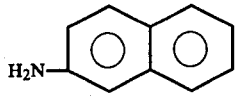 | 14.3 | 200 | 5.0 |
| 5 | 22.0 |  | 10.8 | 200 | 16.0 |
| 6 | 22.0 | 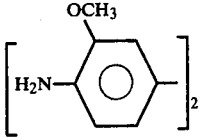 | 12.2 | 200 | 11.0 |
| 7 | 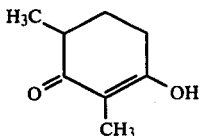 14.0 | 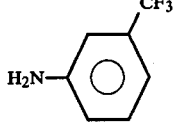 | 16.0 | 200 | 10.0 |

| | | Part 2 | | | |
|---|---|---|---|---|---|
| | | product: | | | |
| Example | structure | melting point (°C.) (solvent for recrystallization) | UV-absorption max (m/μ) | (g) | Yield (% of theory) |
| 1 | (cyclohex-2-enone with N(Et)(Et) at 3-position) | 42-4, bp₀.₀₁Hg=117°-20° C. (—) | 300 | 32.5 | 66 |
| 2 | (3-(4-methoxyphenylamino)cyclohex-2-enone) | 163 (i-PrOH/EtOH) | 300 | 40.0 | 94 |
| 3 | (3-(3-trifluoromethylphenylamino)cyclohex-2-enone) | 158 (EtOH/Et₂O) | 310 | 32.5 | 65 |
| 4 | (3-(2-naphthylamino)cyclohex-2-enone) | 176 (EtOH/ET₂O) | 320 | 12.0 | 50 |
| 5 | (1,4-phenylene-bis(amino-cyclohex-2-enone)) | ≧ 320 (HOAC) | 333 | 24.5 | 83 |
| 6 | (bis compound with OCH₃) | 271-2 (DMF) | 330 | 20.0 | 95 |
| 7 | (6-methoxy-2-methyl-3-(3-trifluoromethylphenylamino)cyclohex-2-enone) | 152 (EtOH) | 319 | 27.9 | 95 | i-PrOH = Iso-propanol
EtOH = ethanol
Et₂O = diethyl ether
HOAC = acetic acid
DMF = formamide formanide

TABLE 2 part 1 catalyst: 0.1 Pd on 0.9 g carbon carrier

| Example | starting material structure | amount (g) | melting point (°C.) | reaction time (min.) | solvent (ml) | temperature (°C.) |
|---|---|---|---|---|---|---|
| 8 | 3-amino-cyclohex-2-enone (NH₂) | 2.0 | 128–31 | 60 | TEG 50 | 193–6 |
| 9 | 3-(N,N-diethylamino)-cyclohex-2-enone | 2.6 | 42–4 | 50 | TEG 50 | 193 |
| 10 | 3-(isopropylamino)-cyclohex-2-enone | 6.0 | 106–7 | 60 | TEG 100 | 204–6 |
| 11 | 3-morpholino-cyclohex-2-enone | 5.0 | 94–5 | 37 | TEG 100 | 205–10 |
| 12 | 3-(3-trifluoromethylanilino)-cyclohex-2-enone | 6.0 | 158 | 50 | TEG 100 | 205–10 |
| 13 | 3-(4-methoxyanilino)-cyclohex-2-enone | 6.5 | 163 | 40 | TEG 100 | 205–10 |
| 14 | 3-anilino-cyclohex-2-enone | 3.0 | 179–81 | 60 | TEG 50 | 214 |
| 15 | 3-(2-naphthylamino)-cyclohex-2-enone | 3.5 | 176 | 60 | TEG 50 | 214 |
| 16 | 1,4-bis(3-oxocyclohex-1-enylamino)benzene | 2.0 | >320 | 30 | TEG 20 | 225–30 |
| 17 | bis[3-(2-methoxyanilino)-cyclohex-2-enone] linked | 2.0 | 272 | 30 | TEG 20 | 225–30 |

TABLE 2-continued part 1 catalyst: 0.1 Pd on 0.9 g carbon carrier

| Example | starting material structure | amount (g) | melting point (°C.) | reaction time (min.) | solvent (ml) | temperature (°C.) |
|---|---|---|---|---|---|---|
| 18 | 5-methyl-2-methyl-3-amino-cyclohex-2-enone | 45.0 | 98–100 | 600 | TEG 200 | 220 |
| 19 | 5-methyl-2-methyl-3-amino-cyclohex-2-enone | 2.0 | 98–100 | 60 | DEG 50 | 185 |
| 20 | 5-methyl-2-methyl-3-(3-trifluoromethylphenylamino)-cyclohex-2-enone | 8.5 | 152 | 50 | TEG 100 | 208–10 | part 2 product:

| Example | structure | yield (g) | (% of theory) | melting point (°C.) | boiling point °C. under mm Hg |
|---|---|---|---|---|---|
| 8 | 3-aminophenol | 1.9 | 95 | 122 | 3^151 |
| 9 | 3-(N,N-diethylamino)phenol | 2.2 | 85 | 78 | |
| 10 | 3-(isopropylamino)phenol | 5.5 | 92 | 100 | |
| 11 | 3-morpholinophenol | 4.5 | 90 | 131 (CHCl$_3$/hexane) | |
| 12 | 3-hydroxy-3'-trifluoromethyl-diphenylamine | 3.6 | 60 | | 2^172–85 |
| 13 | 3-hydroxy-4'-methoxy-diphenylamine | 3.6 | 55 | 83 (CHCl$_3$/hexane) | 0.1^175–7 |
| 14 | 3-hydroxy-diphenylamine | 1.6 | 54 | 80 (CHCl$_3$/hexane) | 0.1^160 |

TABLE 2-continued part 2

| Example | structure | product: yield (g) | (% of theory) | melting point (°C.) | boiling point °C. under mm Hg |
|---|---|---|---|---|---|
| 15 | HO–C₆H₄–NH–naphthyl | 3.0 | 85 | 120 (benzene/hexane) | 0.3²¹² |
| 16 | HO–C₆H₄–NH–C₆H₃(OCH₃)–N(H)–C₆H₄–CH | 1.7 | 85 | 185–6 (CHCl₃/hexane) | |
| 17 | [HO–C₆H₄–NH–C₆H₃(OCH₃)–]₂ | 1.6 | 80 | 163 | |
| 18 | 2,6-dimethyl-3-amino-phenol (H₃C, HO, CH₃, NH₂) | 36.0 | 80 | 104–6 (Et₂O) | 2¹³⁰⁻⁴⁰ |
| 19 | 2,6-dimethyl-3-amino-phenol | 1.8 | 90 | 104–6 | |
| 20 | H₃C–C₆H₂(CH₃)(OH)–NH–C₆H₄–CF₃ | 7.5 | 90 | 48 | 2¹⁷⁰ |

TEG = triethylene glycol diethyl ether
DEG = diethylene glycol diethyl ether

What is claimed is:

1. A process for the manufacture of a 3-aminophenol which comprises dehydrogenating, at a temperature of from 150° to 300° C., a pressure of up to 20 atmospheres and in the liquid phase, a 3-aminocyclohexenone which is a primary or secondary amine.

2. The process defined in claim 1, wherein the 3-aminocyclohexenone is heated in the presence of a dehydrogenation catalyst selected from the group consisting of ruthenium, rhodium, osmium, iridium, platinum, copper, silver, gold, iron, cobalt, palladium and nickel.

3. The process defined in claim 1, wherein the 3-aminocyclohexenone is a secondary amine.

4. The process defined in claim 1, wherein the 3-aminocyclohexenone is a primary amine.

5. The process defined in claim 4, wherein 3-aminocyclohex-2-enone is dehydrogenated.

6. The process defined in claim 4, wherein the dehydrogenation occurs at a pressure of up to one atmosphere.

7. The process defined in claim 4, wherein the dehydrogenation occurs in the presence of a solvent.

8. The process defined in claim 7, wherein triethylene glycol diethyl ether or diethylene glycol diethyl ether is the solvent.

9. The compound N,N'-bis-(3-hydroxyphenyl)-o-dianisidine.

* * * * *